United States Patent [19]
Raffa et al.

[11] Patent Number: 5,336,691
[45] Date of Patent: Aug. 9, 1994

[54] COMPOSITION COMPRISING A TRAMADOL MATERIAL AND ACETAMINOPHEN AND ITS USE

[75] Inventors: Robert B. Raffa, Norristown; Jeffrey L. Vaught, Perkosie, both of Pa.

[73] Assignee: McNeilab, Inc., Spring House, Pa.

[21] Appl. No.: 974,865

[22] Filed: Nov. 10, 1992

Related U.S. Application Data

[63] Continuation-in-part of Ser. No. 755,924, Sep. 6, 1991, abandoned.

[51] Int. Cl.$^5$ ............................................. A61K 31/165
[52] U.S. Cl. ..................................... 514/629; 514/646
[58] Field of Search ................................. 514/629, 646

[56] References Cited

U.S. PATENT DOCUMENTS 3,652,589   3/1972   Flick et al. ...................... 548/578

*Primary Examiner*—Frederick E. Waddell
*Assistant Examiner*—William R. A. Jarvis
*Attorney, Agent, or Firm*—Ralph R. Palo

[57] ABSTRACT

This invention relates to a composition comprising a tramadol material and acetaminophen, and its use. As used herein tramadol refers to various forms of tramadol. The compositions are pharmacologically useful in treating pain and tussive conditions. The compositions are also subject to less opioid side-effects such as abuse liability, tolerance, constipation and respiratory depression. Furthermore, where the components of the compositions are within certain ratios the pharmacological effects of the compositions are superadditive (synergistic).

15 Claims, 1 Drawing Sheet

FIG I
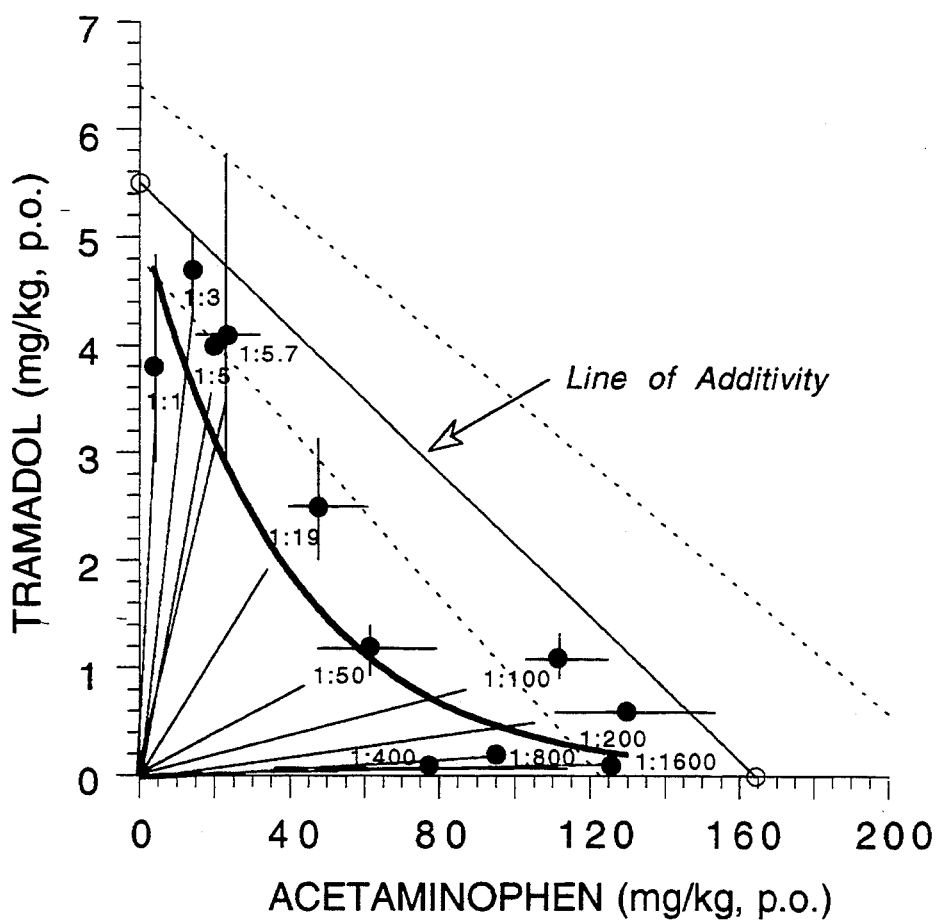

COMPOSITION COMPRISING A TRAMADOL MATERIAL AND ACETAMINOPHEN AND ITS USE

CROSS REFERENCE

This case is related to application Ser. Nos. 7/759,259, filed Sep. 13, 1991, now U.S. Pat. No. 5,223,541 and 07/785,137, filed Oct. 30, 1991, now abandoned, and is a continuation-in-part of application serial No. 07/755,924, filed Sep. 6, 1991, now abandoned.

BACKGROUND OF THE INVENTION

U.S. Pat. No. 3,652,589 discloses a class of analgesic cycloalkanol-substituted phenol esters having a basic amine group in the cycloalkyl ring. The compound (1RS, 2RS)-[(dimethylamino)-methyl]-1-(3-methoxyphenyl)cyclohexanol, commonly known as tramadol, is specifically disclosed therein. A series of articles pertaining to the pharmacology, toxicology and clinical studies of tramadol are found in *Arzneim. Forsch.*, (*Drug Res.*), 28(I), 114 (1978). Driessen et al., *Arch. Pharmacol.*, 341, R104 (1990) disclose that tramadol produces its analgesic effect through a mechanism that is neither fully opioid-like nor non-opioid-like. The Abstracts of the VI th World Congress on Pain, Apr. 1-6 (1990), disclose that tramadol hydrochloride is an orally active pure agonist opioid analgesic. However, clinical experience indicates that tramadol lacks many of the typical side effects of opioid agonists, e.g., respiratory depression (W. -Vogel et al., *Arzneim. Forsch.* (*Drug Res.*), 28(I), 183 (1978)), constipation (I. Arend et al., *Arzneim. Forsch*, (*Drug Res.*), 28(I), 199 (1978)), tolerance (L. Flohe et, al., *Arzneim. Forsch*, (*Drug Res.*), 28(I), 213 (1978)), and abuse liability ( T. Yanagita, *Arzneim. Forsch*, (*Drug Res.*), 28(I), 158 (1978)). When given at a dose of 50 mg by rapid i.v. injection, tramadol may produce certain side effects unique to tramadol including hot flushes and sweating. Despite these side effects, tramadol's combination of non-opioid and opioid activity makes tramadol a very unique drug. Tramadol is currently being marketed by Grunenthal GMBH as an analgesic.

Opioids have for many years been used as analgesics to treat severe pain. They, however, produce undesirable side effects and as a result cannot be given repeatedly or at high doses. The side effect problems are well documented in the literature. See, for example, J. Jaffe and W. Martin in chapter 15, "The Pharmacological Basis of Therapeutics", editors L. Goodman and A. Gilman, 5th Edition, 245 (1975) wherein it is disclosed that morphine and its congeners, e.g., codeine, hydrocodone and oxycodone, are opioid agonist analgesics that exhibit side effects such as respiratory depression, constipation, tolerance and abuse liability.

As alternatives to using opioids, non-opioids such as acetaminophen (APAP) and aspirin are used as analgesics. APAP, like aspirin, is not subject to the tolerance, addiction and toxicity of the opioid analgesics. However, APAP and aspirin are only useful in relieving pain of moderate intensity, whereas the opioid analgesics are useful in relieving more intense pain; See Woodbury, D. and Fingl, E. in "The Pharmacological Basis of Therapeutics", 5th Ed.; Goodman, L. and Gilman, A., Chapter 15, pages 325 (1975).

To reduce the side effect problems of opioids, opioids have been combined with other drugs including non-opioid analgesic agents, which lowers the amount of opioid needed to produce an equivalent degree of analgesia. It has been claimed that some of these combination products also have the advantage of producing a synergistic analgesic effect. For example, A. Takemori, *Annals New York Acad. Sci.*, 281, 262 (1976) discloses that compositions including combinations of opioid analgesics with drugs other than analgesics exhibit a variety of effects, i.e., subadditive (inhibitory), additive or superadditive. R. Taber et al., *J. Pharm. Expt. Thera.*, 169(1), 29 (1969) disclose that the combination of morphine and methadone, another opioid analgesic, exhibits an additive effect. U.S. Pat. No. 4,571,400 discloses that the combination of dihydrocodeine, an opioid analgesic, and ibuprofen, a non-opioid analgesic, provides superadditive effects when the components are within certain ratios. A. Pircio et al., *Arch. Int. Pharmacodyn.*, 235, 116 (1978) report superadditive analgesia with a 1:125 mixture of butorphanol, another opioid analgesic, and acetaminophen (APAP), a non-opioid analgesic, whereas a 1:10 mixture did not show any statistically significant superadditive analgesia.

Combinations of non-opioid analgesics have also been prepared to avoid the side effects associated with opioids, and the combinations are noted to have the benefit of requiring less of each ingredient and in producing superadditive effects. G. Stacher et. al., *Int. J. Clin. Pharmacol. Biopharmacy*, 17, 250 (1979) report that the combination of non-opioid analgesics, i.e., tolmetin and APAP, allows for a marked reduction in the amount of tolmetin required to produce analgesia. In addition, U.S. Pat. No. 4,260,629 discloses that an orally administered composition of APAP and zomepirac, a non-opioid analgesic, in a particular weight ratio range produces a superadditive relief of pain in mammals. Furthermore, U.S. Pat. No. 4,132,788 discloses that 5-aroyl-1-(lower)alkylpyrrole-2-acetic acid derivatives, non-opioid analgesics, when combined with APAP or aspirin exhibit superadditive antiarthritic activity. However, there have been warnings against the daily consumption of non-opioid analgesic mixtures and of the consumption of a single non-opioid analgesic in large amounts or over long periods (see, D. Woodbury and E. Fingl at page 349).

The prior art, however, does not disclose that tramadol an 'atypical' opioid analgesic, can or should be combined with another analgesic to lessen the side effects of each or to yield a composition comprising a tramadol material and another analgesic that exhibits superadditive analgesia.

SUMMARY OF THE INVENTION

It has now been found that a tramadol material which includes various forms of tramadol as defined hereinafter can be combined with APAP to produce analgesia. The combination employs lesser amounts of both the tramadol material and APAP than would be necessary to produce the same amount of analgesia if either was used alone. By using lesser amounts of both drugs the side effects associated with each are reduced in number and degree. Surprisingly, the compositions comprising the tramadol material and APAP have been found to exhibit synergistic analgesic effects when combined in certain ratios. The compositions according to this invention may also be useful in treating tussive conditions.

BRIEF DESCRIPTION OF THE DRAWING

FIG. 1 is an isobologram showing the analgesic effect of tramadol hydrochloride and acetaminophen composition on the acetylcholine-induced abdominal constriction in mice.

DETAILED DESCRIPTION OF THE INVENTION

The present invention is directed to compositions comprising a tramadol material and acetaminophen. The tramadol material is any one of (1R, 2R or 1S, 2S)-(dimethylaminomethyl)-1-(3-methoxyphenyl)-cyclohexanol (tramadol), its N-oxide derivative ("tramadol N-oxide"), and its O-desmethyl derivative ("O-desmethyl tramadol") or mixtures thereof. It also includes the individual stereoisomers, mixtures of stereoisomers, including the racemates, pharmaceutically acceptable salts of the amines, such as the hydrochloride salt, solvates and polymorphs of the tramadol material. Tramadol is commercially available from Grunenthal or may be made by the process described in U.S. Pat. No. 3,652,589, which is herein incorporated by reference.

Tramadol N-oxide is prepared by treating tramadol as a free base with an oxidizing agent, e.g., hydrogen peroxide (30%), in an organic solvent, e.g., methanol or isopropanol, with, bit preferably without heating. See, "Reagents For Organic Synthesis", 1, 471, Fieser & Fieser eds., Wiley N.Y.; (1987), B. Kelentey et al., *Arzneim, Forsch.*, 7, 594 (1957). With heating, the reaction takes about 1 hour, whereas without heating the reaction takes about 3 days. Following the oxidation, the mixture is treated with an agent, e.g. $PtO_2$ or preferably Pt/C, for about a day, to destroy the excess hydrogen peroxide. The mixture is filtered, followed by the evaporation of the filtrate and then the residue is recrystallized from an organic solvent mixture, e.g., methylene chloride/ethyl acetate.

O-Desmethyl tramadol is prepared by treating tramadol as a free base under O-desmethylating reaction conditions, e.g., reacting it with a strong base such as NaH or KH, thiophenol and diethylene glycol (DEG) with heating to reflux. See, Wildes et al., *J. Org. Chem.*, 36, 721 (1971). The reaction takes about an hour, followed by the cooling and then quenching in water of the reaction mixture. The quenched mixture is acidified, extracted with an organic solvent such as ethyl ether, basified and then extracted with a halogenated organic solvent such as methylene chloride. The extract is then dried and the solvent evaporated to yield the O-desmethyl product, which may then be short-path distilled, converted to its corresponding salt, e.g., treated with an acidified (HCl/ethanol) solution, and recrystallized from an organic solvent mixture, e.g., ethanol/ethyl ether.

The pharmacology of acetaminophen is reviewed by B. Ameer et al., *Ann. Int. Med.*, 87, 202 (1977), and the preparation of acetaminophen is disclosed in U.S. Pat. No. 2,998,450, which is incorporated herein by reference.

The APAP and the tramadol material are generally present in a weight ratio of tramadol material to APAP from about 1:1 to 1:1600. Certain ratios result in a composition which exhibits synergistic analgesic effects. For example, in a composition comprising a tramadol material and APAP, the ratio of the tramadol material:APAP is preferably from about 1:5 to 1:1600; and, more preferably, from about 1:19 to 1:800.

The most preferred ratios are from about 1:19 to 1:50. Compositions of a tramadol material and APAP within these weight ratios have been shown to exhibit synergistic analgesic effects. In addition, the particular compositions wherein the ratio of the components are about 1:1 and about 1:5 are encompassed by the present invention.

The tramadol/APAP formulations according to the present invention may also contain therapeutically effective amounts of one or more other pharmaceutical actives including but not limited to decongestants or bronchodilators (such as pseudoephedrine, phenylpropanolamine, phenylephrine and pharmaceutically acceptable salts thereof), antitussives (such as caraminophen, dextromethorphan and pharmaceutically acceptable salts thereof), antihistamines (such as chlorpheniramine, brompheniramine, dexchlorpheniramine, dexbromphreniramine, triprolidine, doxylamine, tripelennamine, cyproheptadine, hydroxyzine, pyrilamine, azatadine, promethazine and pharmaceutically acceptable salts thereof), non-sedating antihistamines (such as acrivastine, astemizole, cetirizine, ketotifen, loratidine, temelastine, terfenadine (including the metabolites disclosed in U.S. Pat. No. 4,254,129 and 4,284,957 hereby incorporated by reference) and pharmaceutically acceptable salts thereof), muscle relaxants (such as glycerylmonether SMRS, methocarbamol, mephenesin, mephenesin carbamate, mephenesin acid succinate, cyclobenzaprine, chlorphenesin carbamate, chlorzoxazone or pharmceutically acceptable salts thereof) and suspected adjuvants (such as diphenhyhdramine, caffeine, xanthine derivatives (including those disclosed in U.S. Pat. No. 4,558,051, hereby incorporated by reference) and pharmaceutically acceptable salts thereof) and combinations of any of the aforesaid pharmaceuticals. The aforesaid pharmaceuticals may be combined with a tramadol/acetaminophen formulation for the treatment of such ailments as allergies, sleep disorders, cough, colds, cold-like and/or flu symptoms in mammals including humans.

Pharmaceutical compositions comprising the tramadol material and acetaminophen and when desired other pharmaceutical actives in an intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in an oral dosage form, any of the usual pharmaceutical media may be employed. For example, in the case of oral liquid preparations (such as suspensions, elixirs and solution), water, glycols, oils, alcohols, flavoring agents, preservatives, coloring agents and the like may be used. In the case of oral solid preparations (such as, for example, powders, capsules and tablets), carriers such as starches, sugars, diluents, granulating agents, lubricants, binders, disintegrating agents and the like, may be used. Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally be in the form of a dosage unit, e.g., tablet, capsule, powder, injection, teaspoonful and the like, containing from 0.1 to about 800 mg/kg, and preferably from about 0.3 to 200 mg/kg of the active ingredients. The dosage unit is calculated based on the amount of active which may be given to a 70 kg human subject in a single dose. The pharmaceutical compositions may be given at a daily dosage of from about 10 to 6000 mg/kg/day. However, it will be appreciated that the precise dose of the active ingredients will vary depending upon the relative amounts of active components being used. In the case wherein one or more other pharmaceutical components are added to the tramadol/APAP composition those components may be added in amounts known in the art and may be given at dosages conventional for such components. For example, decongestants and bronchodilators may be given in a single dosage of from about 12.5 to 75 mg/kg and at a daily dosage of from about 60 to 150 mg/kg/day. Antitussives may be given in a single dosage of from about 2.5 to 30 mg/kg and at a daily dosage of from about 20 to 120 mg/kg/day. Antihistamines may be given in a single dosage of from about 1 to 50 mg/kg and at a daily dosage of from about 4 to 600 mg/kg/day. Non-sedating antihistamines may be given in a single 1 dosage of from about 8 to 30 mg/kg and at a daily dosage of from about 30 to 120 mg/kg/day. Muscle relaxants may be given at a single dosage of from about 10 to 1500 mg/kg and at a daily dosage of from about 60 to 8000 mg/kg/day. Adjuvants may be given in a single dosage of from about 1 to 25 mg/kg and at a daily dosage of from about 1 to 100 mg/kg/day.

The following experimental examples describe the invention in greater particularity and are intended to be a way of illustrating but not limiting the invention.

EXAMPLE 1

Preparation of the Combined Doses of Tramadol and APAP

The preparation of different ratios of a tramadol-/APAP combination is effected by first preparing a stock solution of tramadol having a concentration expressed in $mg_{drugs}$ per 10 mL of distilled water. For example, 8 mg of tramadol as the free base is dissolved per 10 mL of water to yield the highest dose of tramadol stock solution. The stock solution of the tramadol is then diluted with a sufficient amount of distilled water to prepare the lower doses of the tramadol per 10 mL of distilled water. The combinations are then made by adding 10 mL of each dilution to the appropriate mg of APAP to achieve the desired ratio of tramadol to APAP. For the 1:50 example: 400 mg of APAP as the free base is suspended with 10 mL of the 8 mg tramadol solution and 2 drops of TWEEN 80, a pharmacological dispersant, manufactured by Fisher Scientific Company, to yield the 1:50 ratio, i.e., (8 mg: 400 mg) combination per 10 mL of water. Each ratio was prepared separately in a similar manner and injected in a volume of 10 mL/kg per mouse.

EXAMPLE 2

Preparation of the Combined Doses of Tramadol N-oxide and APAP

First, tramadol N-oxide was prepared as set forth hereinafter. Tramadol hydrochloride (0.5 mol) was converted to its free base in basified water (pH >9) and then extracted with ether. The ether was evaporated to yield the crystalline hydrate of tramadol. The solid was then heated with steam under a high vacuum to remove as much water as possible to yield 131.5 g of material. The material was dissolved in methanol (500 mL) and 65 g of 30% $H_2O_2$ was added. The solution was stirred for 3 hours and then an additional 65 g of the 30% $H_2O_2$ was added. The reaction was stirred for 2.5 days at room temperature. Approximately 10 mg of $PtO_2$ on carbon (use of Pt/C is suggested for its ease of removal) was added to the reaction mixture, and very gentle foaming took place. An additional 10 mg of $PtO_2$ was added and the reaction mixture was stirred overnight and then filtered thru a filter aid. The filtrate was concentrated under vacuum while being heated to a temperature of <40° C. The residue was taken up in methylene chloride. Since the methylene chloride solution contained some colloidial platinum, the solution was diluted with ethyl acetate to 1 L and filtered through a nylon filter membrane (0.45μ pore size) to yield a clear colorless filtrate. The filtrate was concentrated to 600 mL, and then ethyl acetate was added continuously to maintain a volume of 800 mL while the solution was heated until a vapor temperature of 74° C. was reached. The solution was then cooled to room temperature. The solid was collected by filtration, washed with ethyl acetate and dried in vacuo to yield 126.6 g of the tramadol N-oxide (mp. 159.5°–160° C.).

C16H25NO3 Theor.: C, 68.78; H, 9.27; N, 5.01 Found: C, 68.65; H, 9.22; N, 4.99

The preparation of different ratios of a tramadol N-oxide/APAP combination is effected by first preparing a stock solution of tramadol-N-oxide having a concentration expressed in $mg_{drugs}$ per 10 mL of distilled water. For example, 8 mg of tramadol N-oxide as the free base is dissolved per 10 mL of water to yield the highest dose of tramadol stock solution. The stock solution of the tramadol-N-oxide is then diluted with a sufficient amount of distilled water to prepare the lower doses of the tramadol N-oxide per 10 mL of distilled water. The combinations are then made by adding 10 mL of each dilution to the appropriate mg of APAP to achieve the desired ratio of tramadol N-oxide to APAP. For the 1:50 example: 400 mg of APAP as the free base is suspended with 10 mL of the 8 mg tramadol N-oxide solution and 2 drops of TWEEN 80, a pharmacological dispersant, manufactured by Fisher Scientific Company, to yield the 1:50 ratio, i.e., (8 mg: 400 mg) combination per 10 mL of water. Each ratio was prepared separately in a similar manner and injected in a volume of 10 mL/kg per mouse.

Example 3

(−) and (+) Enantiomers of O-Desmethyl Tramadol: Their Syntheses and the Preparation of Doses of O-Desmethyl Tramadol-with APAP First, O-desmethyl tramadol was prepared as set forth hereinafter. Diethylene glycol(125 mL) was added with cooling to potassium hydride (9.5 g) with the temperature being maintained at <50° C. To the solution was added thiophenol (10 mL) dissolved in diethylene glycol (25 mL), and then (−)-tramadol as the free base (9.3 g) in diethylene glycol (50 mL) was added. The final reaction mixture was heated slowly to reflux for 45 minutes. The mixture was cooled and then quenched into water. The pH was adjusted to about 3, and the mixture was extracted with ethyl ether. The pH was readjusted to about 8 and the resulting mixture was extracted 5 more times with methylene chloride. The extract was dried and the methylene chloride was evaporated to yield 4.6 g of the title compound as an oil. The oil was distilled (Kugelrohr), dissolved in tetrahydrofuran, treated with an ethanol/HCl solution to give 2.3 g of the salt. The salt was recrystallized from ethanol-/ethyl ether and dried to yield 1.80 g of the salt of the (−) enantiomer of O-desmethyl tramadol (mp. 242°-3° C.), $[\alpha]_D^{25} = -32.9$ (C=1, EtOH).

C15H23NO2.HCl Theor.: C, 63.04; H, 8.46; N, 4.90 Found: C, 63.00; H, 8.51; N, 4.94

To prepare the (+) enantiomer of the title compound, the reaction was run under the same conditions except that (+)-tramadol as the free base was used instead of the (−)-tramadol to yield 2.8 g of the (+) enantiomer of O-desmethyl tramadol (mp. 242°-3° C.) $[\alpha]_D^{25} = +32.2$ (C=1, EtOH).

C15H23NO2.HCl Theor.: C, 63.04; H, 8.46; N, 4.90 Found: C, 63.14; H, 8.49; N, 4.86

The preparation of different ratios of a O-desmethyl-/APAP combination is effected by first preparing a stock solution of O-desmethyl tramadol having a concentration expressed in mg$_{drugs}$ per 10 mL of distilled water. For example, 8 mg of O-desmethyl tramadol as the free base is dissolved per 10 mL of water to yield the highest dose of O-desmethyl tramadol stock solution. The stock solution of the O-desmethyl tramadol is then diluted with a sufficient amount of distilled water to prepare the lower doses of the O-desmethyl tramadol per 10 mL of distilled water. The combinations are then made by adding 10 mL of each dilution to the appropriate mg of APAP to achieve the desired ratio of O-desmethyl tramadol to APAP. For the 1:50 example: 400 mg of APAP as the free base is suspended with 10 mL of the 8 mg O-desmethyl tramadol solution and 2 drops of TWEEN 80, a pharmacological dispersant, manufactured by Fisher Scientific Company, to yield the 1:50 ratio, i.e., (8 mg: 400 mg) combination per 10 mL of water. Each ratio was prepared separately in a similar manner and injected in a volume of 10 ml/kg per mouse.

EXAMPLE 4

Analgesic Activity

Male CD1 mice (weighing from 18–24 g) were utilized in determining the analgesic effects associated with the compositions of the invention. The mice were all dosed orally with tramadol hydrochloride (calculated as the base), which was completely dissolved in distilled water, and acetaminophen (calculated as the base), which was completely dissolved in distilled water or in distilled water containing 2% by volume of Tween 80 containing 100% polysorbate 80. The dosing volume was 10 mL/kg.

The procedure used in detecting and comparing the analgesic activity of different classes of analgesia drugs for which there is a good correlation with human efficacy is the prevention of acetylcholine-induced abdominal constriction in mice (H. Collier et al., Br. J. Pharmacol., 32, 295 (1968)).

Mice, intubated with various doses of tramadol hydrochloride alone, acetaminophen alone, combined doses of tramadol hydrochloride and acetaminophen, or vehicle such as distilled water, or distilled water containing 2% by volume of Tween 80, were injected intraperitoneally with a challenge dose of acetylcholine bromide. The acetylcholine was completely dissolved in distilled water at a concentration of 5.5 mg/kg and injected at the rate of 0.20 mL/20 g. For scoring purposes an "abdominal constriction" was defined as a contraction of the abdominal musculature accompanied by arching of the back and extension of the limbs. The mice were observed 10 minutes for the presence or absence of the abdominal constriction response beginning immediately after receiving the acetylcholine dose, which was 30 minutes after receiving the oral administration of tramadol hydrochloride, acetaminophen, combined doses of tramadol hydrochloride and acetaminophen, or vehicle. Each mouse was used only once.

The analysis of possible superadditivity for the compositions at each fixed ratio was determined as disclosed by R. J. Tallarida et al., Life Sci., 45, 947 (1989). This procedure involved the determination of the total amount in the mixture that is required to produce a specified level of effect, such as 50% (ED50$_{mix}$), and the corresponding total amount that would be expected under simple additivity (ED50$_{add}$). Where it was established that ED50$_{mix}$ < ED50$_{add}$ for a specific fixed-ratio, then that composition ratio was superadditive. Both the quantities ED50$_{mix}$ and ED50$_{add}$ were random variables; ED50$_{mix}$ was estimated from the dose-response curve for a specific fixed-ratio; ED50$_{add}$ was obtained by combining the ED50 estimates for the two drugs under additivity. ED50$_{mix}$ was then compared to ED50$_{add}$ via a Student's t-test. The ED50 value for tramadol hydrochloride alone was 5.5(4.8–6.4) mg/kg. The ED50 value for acetaminophen alone was 164.3 (122.7–219.9) mg/kg.

The interaction between tramadol and acetaminophen was determined at precise dosage ratios of tramadol hydrochloride and acetaminophen. Multiple (typically 4–6) coded doses of each selected combination were studied for analgesic effectiveness after 30 minutes using an experimental design which permitted the complete randomization of the separate dosage forms tested.

The interaction of tramadol hydrochloride and acetaminophen on the acetylcholine-induced abdominal constriction in mice was demonstrated by the data in Table I and is shown in the Loewe isobologram, FIG. I, (see, S. Loewe, Pharm. Rev., 9; 237 (1957) regarding the preparation and basis of an isobologram). In FIG. 1, the diagonal line joining the ED50 values of the two drugs given separately represents the simple additivity of effects at different component ratios. The dotted lines adjacent to the diagonal line define the 95% confidence interval. ED50 values falling under the curve (between the line and the origin) indicate superadditivity, i.e., unexpected enhancement of effects. The diagonal dashed lines radiating from the origin represent the dose ratios of APAP to tramadol hydrochloride used in mice receiving the combined drug dosages. The bars through the ED50 points for the tramadol and APAP composition represent the 95% confidence intervals of the ED50 value. The experimental data as represented in FIG. I establishes that compositions having a ratio of tramadol to APAP from 1:1 to 1:1600 (represented by the curved line) give unexpectedly enhanced activity since ED50$_{mix}$ is less than ED50$_{add}$.

TABLE I

| DRUG COMBINATIONS (Tramadol:APAP) | TRAMADOL:APAP DOSE (mg/kg, p.o.) | | analgesia | $ED_{50}$ 30 min (95% CI's) | |
|---|---|---|---|---|---|
| | Tramadol | APAP | | Tramadol | APAP |
| tramadol only | 2 | 0 | 3/15 | | |
| | 3 | 0 | 4/15 | | |
| | 4 | 0 | 14/45 | | |
| | 6 | 0 | 20/45 | 5.5 | |
| | 8 | 0 | 40/60 | (4.8–6.4) | |
| | 10 | 0 | 15/15 | | |
| | 16 | 0 | 14/15 | | |
| 1000:1 | 3.75 | 0.00375 | 1/13 | | |
| | 7.5 | 0.0075 | 8/15 | 7.0 | 0.01 |
| | 15 | 0.015 | 15/15 | (5.7–8.4) | (0.1–0.1) |
| 100:1 | 1.875 | 0.01875 | 0/15 | | |
| | 3.75 | 0.0375 | 4/15 | 6.9 | 0.1 |
| | 7.5 | 0.075 | 5/15 | (5.2–9.0) | (0.1–0.1) |
| | 15 | 0/15 | 15/15 | | |
| 20:1 | 1.875 | 0.09375 | 0.15 | | |
| | 3.75 | 0.1875 | 4/15 | 6.5 | 0.3 |
| | 7.5 | 0.375 | 7/15 | (5.1–8.3) | (0.3–0.4) |
| | 15 | 0.75 | 15/15 | | |
| 3:1 | 3.75 | 1.25 | 3/30 | | |
| | 7.5 | 2.5 | 12/30 | 7.8 | 2.6 |
| | 15 | 5 | 28/30 | (6.6–9.1) | (2.2–3.0) |
| 1:1 | 0.94 | 0.94 | 3/15 | | |
| | 1.875 | 1.875 | 8/30 | | |
| | 3.75 | 3.75 | 14/30 | 3.8 | 3.8 |
| | 5 | 5 | 12/28 | (3.0–4.8) | (3.0–4.8) |
| | 7.5 | 7.5 | 24/30 | | |
| | 15 | 15 | 15/15 | | |
| 1:3 | 3.75 | 11.25 | 7/30 | | |
| | 5 | 15 | 7/15 | 4.7 | 14.2 |
| | 7.5 | 22.5 | 29/30 | (4.3–5.2) | (12.8–15.7) |
| 1:5 | 2.5 | 12.5 | 7/30 | | |
| | 5 | 25 | 8/30 | 4.0 | 19.8 |
| | 10 | 50 | 30/30 | (3.3–4.7) | (16.7–23.4) |
| 1:5.7 | 0.47 | 2.66 | 0/15 | | |
| | 0.94 | 5.313 | 4/15 | | |
| | 1.88 | 10.625 | 1/15 | 4.1 | 23.3 |
| | 3.75 | 21.25 | 5/15 | (3.0–5.7) | 16.8–32.3) |
| | 7.5 | 42.5 | 11/15 | | |
| | 15 | 85 | 15/15 | | |
| 1:19 | 0.94 | 17.813 | 4/30 | | |
| | 1.88 | 36.625 | 10/28 | | |
| | 3.75 | 71.25 | 21/30 | 2.5 | 47.3 |
| | 5 | 95 | 22/30 | (2.0–3.0) | (38.9–57.5) |
| | 7.5 | 142.5 | 29/30 | | |
| | 15 | 285 | 15/15 | | |
| 1:50 | 0.25 | 12.5 | 3/30 | | |
| | 0.5 | 25 | 7/30 | | |
| | 1 | 50 | 9/30 | 1.2 | 61.4 |
| | 2 | 100 | 19/30 | (1.0–1.5) | (49.0–77.1) |
| | 4 | 200 | 27/30 | | |
| | 8 | 400 | 30/30 | | |
| 1:100 | 0.25 | 25 | 3/60 | | |
| | 0.5 | 50 | 12/60 | | |
| | 1 | 100 | 19/60 | 1.1 | 111.3 |
| | 2 | 200 | 51/60 | (1.0–1.3) | (96.4–128.6) |
| | 4 | 400 | 55/60 | | |
| | 8 | 800 | 30/30 | | |
| 1:200 | 0.125 | 25 | 1/60 | | |
| | 0.25 | 50 | 9/60 | | |
| | 0.5 | 100 | 27/60 | 0.6 | 129.7 |
| | 1 | 200 | 44/60 | (0.6–0.8) | (110.4–152.4) |
| | 2 | 400 | 48/60 | | |
| | 4 | 800 | 30/30 | | |
| 1:400 | 0.0625 | 25 | 2/15 | | |
| | 0.125 | 50 | 4/30 | | |
| | 0.25 | 100 | 18/30 | 0.2 | 95.1 |
| | 0.5 | 200 | 12/15 | (0.2–0.3) | (75.4–119.8) |
| | 1 | 400 | 28/30 | | |
| | 2 | 800 | 15/15 | | |
| 1:800 | 0.03125 | 25 | 4/30 | | |
| | 0.0625 | 50 | 9/30 | | |
| | 0.125 | 100 | 15/30 | 0.1 | 77.4 |
| | 0.25 | 200 | 27/30 | (0.1–0.1) | (62.9–95.2) |
| | 0.5 | 400 | 30/30 | | |
| 1:1600 | 0.03125 | 50 | 2/30 | | |
| | 0.0625 | 100 | 14/30 | | |
| | 0.125 | 200 | 22/30 | 0.1 | 125.7 |
| | 0.25 | 400 | 27/30 | (0.1–0.1) | (102.7–153.8) |

TABLE I-continued

| DRUG COMBINATIONS (Tramadol:APAP) | TRAMADOL:APAP DOSE (mg/kg, p.o.) | | | ED$_{50}$ 30 min (95% CI's) | |
|---|---|---|---|---|---|
| | Tramadol | APAP | analgesia | Tramadol | APAP |
| | 0.5 | 800 | 30/30 | | |
| APAP only | 0 | 30 | 2/15 | | |
| | 0 | 40 | 12/43 | | |
| | 0 | 50 | 1/15 | | |
| | 0 | 60 | 8/30 | | |
| | 0 | 80 | 23/60 | | |
| | 0 | 100 | 13/30 | — | 164.3 |
| | 0 | 120 | 13/30 | | (122.7–219.9) |
| | 0 | 160 | 10/30 | | |
| | 0 | 200 | 13/25 | | |
| | 0 | 240 | 14/25 | | |
| | 0 | 400 | 12/15 | | |
| | 0 | 800 | 13/15 | | |

We claim:

1. A pharmaceutical composition comprising a tramadol material and acetaminophen, wherein the ratio of the tramadol material to acetaminophen is a weight ratio from about 1:1 to about 1:1600.

2. The pharmaceutical composition of claim 1 wherein the tramadol material is tramadol hydrochloride.

3. The pharmaceutical composition of claim 2 wherein the tramadol hydrochloride is racemic.

4. The pharmaceutical composition of claim 1 wherein the weight ratio is about 1:1.

5. The pharmaceutical composition of claim 1 wherein the weight ratio is from about 1:5 to about 1:1600.

6. The pharmaceutical composition of claim 5 wherein the weight ratio is about 1:5.

7. The pharmaceutical composition of claim 5 wherein the weight ratio is from about 1:19 to about 1:800.

8. The pharmaceutical composition of claim 7 wherein the weight ratio is from about 1:19 to about 1:50.

9. The pharmaceutical composition of claim 1 further comprising a pharmaceutically acceptable carrier.

10. The pharmaceutical composition of claim 1 further comprising a decongestant or bronchodilator.

11. The pharmaceutical composition of claim 1 further comprising an antitussive.

12. The pharmaceutical composition of claim 1 further comprising an antihistamine or a non-sedating antihistamine.

13. The pharmaceutical composition of claim 1 further comprising a muscle relaxant.

14. The pharmaceutical composition of claim 1 further comprising a sleep aid.

15. A method for treating a pain in a mammal comprising an administration to the mammal an effective amount of the pharmaceutical composition of claim 1.

* * * * *